United States Patent
Kreye et al.

(10) Patent No.: US 7,247,750 B2
(45) Date of Patent: *Jul. 24, 2007

(54) PROCESS FOR PREPARING (R)-SALBUTAMOL

(75) Inventors: Paul Kreye, Ingelheim (DE); Alfons Lenhart, Weiler (DE); Franz Dietrich Klingler, Griesheim (DE)

(73) Assignee: Boehringer Ingelheim Pharma GmbH & Co. KG, Ingelheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 11/332,418

(22) Filed: Jan. 13, 2006

(65) Prior Publication Data

US 2006/0122431 A1 Jun. 8, 2006

Related U.S. Application Data

(63) Continuation of application No. 10/692,060, filed on Oct. 23, 2003, now Pat. No. 7,049,469.

(60) Provisional application No. 60/499,514, filed on Sep. 2, 2003.

(30) Foreign Application Priority Data

Oct. 24, 2002 (DE) .............................. 102 49 576

(51) Int. Cl.
*C07B 211/00* (2006.01)

(52) U.S. Cl. ...................................... 564/304; 564/358

(58) Field of Classification Search ................ 564/304, 564/358

See application file for complete search history.

(56) References Cited

FOREIGN PATENT DOCUMENTS

| EP | 0 678 503 | 10/1995 |
| WO | WO 95/29146 A1 | 11/1995 |
| WO | WO 00/43345 A1 | 7/2000 |

OTHER PUBLICATIONS

Sakuraba, S. et al; Efficient Asymmetric Hydrogenation of Alfa-Amino Ketone Derivatives. A Highly Enantioselective Synthesis of Phenylephrine, Levamisole, Carnitine and Propranolol; Chemical and Pharmaceutical Bulletin, Pharmaceutical Society of Japan: Bd. 43, Nr. 5, pp. 738-747.

Herold, P., et al. "A Versatile and Stereocontrolled Synthesis of Hydroxyethylene Dipeptide Isosters", Journal of Organic Chemistry, vol. 54, No. 5, (Mar. 1989), pp. 1178-1185.

Cahiez, G., et al. "Highly Stereo- and Chemoselective Iron-Catalyzed Alkenylation of Organomagnesium Compounds", Synthesis, No. 8 (Aug. 1998), pp. 1199-1200.

*Primary Examiner*—Samuel Barts
(74) *Attorney, Agent, or Firm*—Michael P. Morris; Philip I. Datlow; Mary-Ellen M. Devlin

(57) ABSTRACT

Disclosed are processes for preparing levosalbutamol or the pharmacologically acceptable salts thereof on an industrial scale, using asymmetric hydrogenation as the key step and optionally a special sequence of subsequent steps, using rhodium as catalyst and a chiral bidentate phosphine ligand such as (2R, 4R)-4-(dicyclohexylphosphino)-2-(diphenylphosphino-methyl)-N-methyl-aminocarbonyl-pyrrolidine as catalyst system.

25 Claims, No Drawings

PROCESS FOR PREPARING (R)-SALBUTAMOL

APPLICATION DATA

This application is continuation of U.S. Nonprovisional application Ser. No. 10/692,060, filed Oct. 23, 2003, now U.S. Pat. No. 7,049,469, which claims benefit to German application DE 102 49 576 filed Oct. 24, 2002 and U.S. provisional application 60/499,514 filed Sep. 2, 2003.

FIELD OF INVENTION

The present invention relates to an improved process for preparing (R)-salbutamol by rhodium-catalysed asymmetrical hydrogenation on an industrial scale.

TECHNICAL BACKGROUND TO THE INVENTION (R)-Salbutamol, levosalbutamol or (R)-albuterol is α-[[(1,1-dimethylethyl)-amino]methyl-4-hydroxy-1,3-benzenedimethanol, belongs to the β-2-agonists used pharmaceutically as bronchodilators and is of considerable commercial interest. The chemical structure of the chiral α-aminoalcohol (R)-salbutamol is shown in formula I:

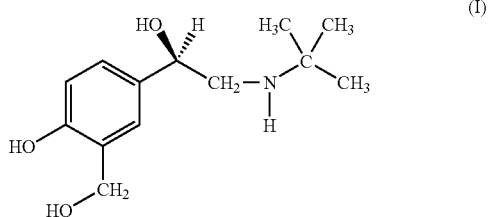

The methods of preparing (R)-salbutamol known in the art include the racemate cleaving of racemic salbutamol using di-toluyltartaric acid, e.g. according to U.S. Pat. No. 5,399,765. In addition, International Patent Application WO 95/29146 proposes the preparation of (R)-salbutamol starting from corresponding alpha-iminoketone by enantioselective reduction with boranes in the presence of a chiral oxaborazole catalyst.

However, the processes described in the art are not suitable for preparing (R)-salbutamol on an industrial scale as half the valuable starting product is lost during the racemate cleaving and large amounts of the oxaborazole catalyst, which is difficult to obtain, have to be used during the enantioselective reduction.

One of the primary objectives of the present invention is to develop a process by means of which (R)-salbutamol can be prepared with a high degree of optical and chemical purity. This is intended, for example, to minimise the danger of drugs which contain (R)-salbutamol as active substance being contaminated with the unwanted D-enantiomer.

Another aim of the invention is to develop a process by means of which (R)-salbutamol can easily be prepared in substantially enantiomerically pure form from starting materials which are easily obtained.

Another aim of the invention is to prepare (R)-salbutamol by means of a stereoselective process in order to avoid reaction steps in which chiral intermediate compounds or the chiral end product (R)-salbutamol is obtained as a racemate in a similar amount to the corresponding antipode.

Surprisingly it has now been found that (R)-salbutamol can be obtained on an industrial scale in very good yields and with good optical purity if salbutamone is subjected to asymmetric hydrogenation in the presence of rhodium and a chiral, bidentate phosphine ligand as catalyst system.

DESCRIPTION OF THE INVENTION

The present invention relates to a process for preparing levosalbutamol or (R)-salbutamol or the pharmacologically acceptable salts thereof starting from prochiral salbutamone as educt, in which salbutamone is subjected to asymmetric hydrogenation in the presence of rhodium and a chiral bidentate phosphine ligand (PP*), particularly (2R,4R)-4-(dicyclohexylphosphino)-2-(diphenylphosphino-methyl)-N-methyl-aminocarbonyl-pyrrolidine, as catalyst system, and the levosalbutamol obtained is optionally converted into a salt with an acid.

In a preferred process the asymmetric hydrogenation is carried out in a temperature range from 20° C. to 100° C., preferably from 40° C. to 60° C., particularly from 45° C. to 55° C.

Also preferred is a process in which the asymmetric hydrogenation is carried out under a pressure of more than 1 bar to 100 bar, preferably under a pressure of 10 bar to 50 bar, particularly at about 20 bar.

The reaction media used may be both protic solvents—such as e.g. alcohols and/or water or aprotic polar solvents such as e.g. ethers and/or amides or lactams and/or mixtures thereof. Water may optionally be added to all the solvents. The protic solvents used are preferably branched or unbranched $C_1$-$C_8$ alkanols. Particularly preferably, lower alcohols such as methanol, ethanol, n-propanol and isopropanol or mixtures thereof are used. Methanol is particularly preferably used as the reaction medium, while the methanol or the other alcohols or solvents may optionally contain water. Suitable aprotic solvents are polar ethers such as for example tetrahydrofuran or dimethoxyethylether or amides such as for example dimethylformamide, or lactams such as for example N-methylpyrrolidone. Preferably, solvents with a slight tendency to flammability are used.

The reaction is preferably carried out in the presence of a base. The base used may be an organic base or an inorganic bases both in solid form and also in the form of solutions, e.g. aqueous solutions. Suitable inorganic bases are basically reacting alkali metal salts or alkali metal hydroxides. Preferably, alkali metal hydrogen carbonates or alkali metal carbonates are used in addition to alkali metal hydroxides. Most preferably, $Na_2CO_3$, $K_2CO_3$, LiOH, NaOH, KOH or $NaHCO_3$ is used.

Suitable organic bases are tertiary amines, particularly tertiary alkyl-amines, tertiary alkyl-aryl-amines or pyridines. Preferably trialkylamines with branched or unbranched $C_1$-$C_5$-alkyl groups are used. Triethylamine or diisopropylethylamine have proved particularly preferable for example. If desired the reaction may also be carried out in the presence of basic polymers with e.g. tertiary amino functions.

Preferred methods are those wherein salbutamone is used in a molar ratio to the rhodium catalyst of from 500:1 to 100000:1, preferably from 750:1 to 20000:1 during asymmetric hydrogenation.

With a molar ratio of catalyst to substrate of about 1:1000 (R)-salbutamol is obtained in an optical purity of 70% ee by the process according to the invention starting from salbutamone (reaction plan 1). By converting the salbutamol (I) into an acid addition salt and subsequently precipitating it from an ammonia-methanol-water mixture the optical purity can be further increased in a simple and remarkable manner.

It has also been found that, in contrast to the teaching of WO 95/29146, there is no need to have a molar ratio of catalyst to substrate of about 1:10, as disclosed therein, for the asymmetric reduction in order to obtain good yields or high optical purity. In the process according to the invention this ratio can be drastically lowered by a factor of 10 to 1000. In spite of this significant reduction in the amount of catalyst the (R)-salbutamol resulting from the asymmetric hydrogenation is still obtained in a significantly higher optical yields than by the process known from the prior art. The reduction in the amount of catalyst makes it much easier to purify the product.

By reducing the amount of catalyst and using the commercially favourable salbutamone as educt the costs of producing (R)-salbutamol can be reduced substantially by the new process.

The salbutamone to be used as starting product is obtained by hydrogenation of N-benzylsalbutamone, which may be prepared by brominating 4-acetyloxy-3-acetyloxymethyl-benzophenone and subsequently reacting with tert-butyl-benzylamine (TBBA) according to the following reaction plan:

Reaction Plan

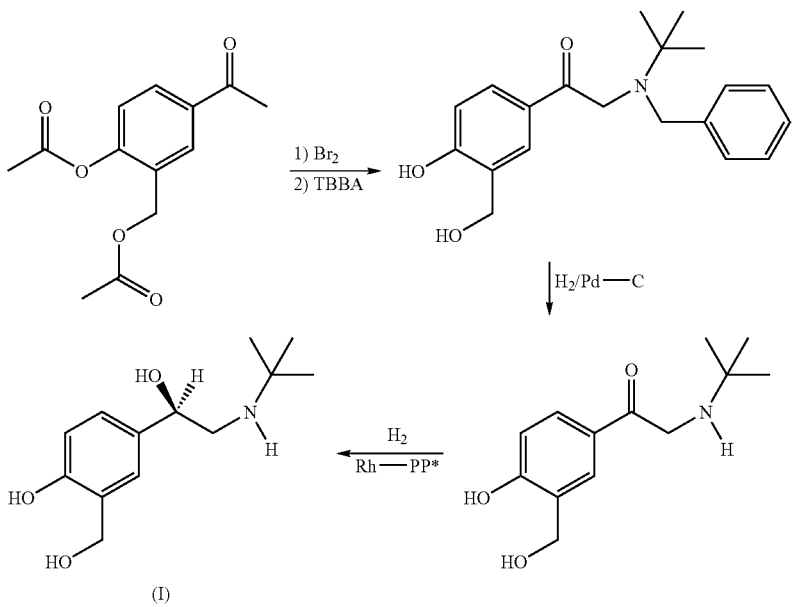

(I)

In addition, the space-time yield can be improved over that of the prior art using the new process. It is particularly advantageous for preparing (R)-salbutamol on an industrial scale from the point of view of costs and safety.

Finally, it is possible using the process according to the invention to do away with the protection of the phenolic hydroxyl group in salbutamone and still successfully react it to obtain chiral (R)-salbutamol using asymmetric hydrogenation with one of the catalyst systems according to the invention.

According to the invention the catalyst used is [Rh(COD) Cl]$_2$, where COD denotes a cyclooctadienyl group, and a chiral, bidentate phosphine ligand (PP*). Preferably (2R, 4R)-4-(dicyclohexylphosphino)-2-(diphenylphosphino-methyl)-N-methyl-aminocarbonylpyrrolidine (RR-MCCPM) is used as catalyst.

The preparation of this catalyst is known from the prior art [EP-A-0 251 164, EP-A-0 336 123]. The catalyst may also be bound to the polymer, e.g. by having the chiral ligand (2R,4R)-4-dicyclohexylphosphino)-2-(diphenylphosphino-methyl)-N-methyl-aminocarbonyl) pyrrolidine bound to a polymer via the phenyl groups, for example. The use of such polymer-bound ligands does not totally rule out the simultaneous use of non-polymer-bound ligands. Such polymer-bound catalysts are particularly advantageous for simple purification of the product.

The catalyst is either used as a prefabricated, oxygen-free solution of [Rh(COD)Cl]$_2$ and ligand or prepared in situ from [Rh(COD)Cl]$_2$ and ligand in the presence of salbutamone without oxygen in a protective gas atmosphere or hydrogen atmosphere.

The hydrogenation is generally carried out without oxygen, conveniently under inert gas, preferably under a hydrogen atmosphere. However, it is not essential to the reaction that the hydrogen for the hydrogenation should be capable of being taken from the atmospheric gas above the reaction mixture. The hydrogen may also be produced in solution in situ from suitable hydrogen sources. Such hydrogen sources include e.g. ammonium formate, formic acid and other formates, hydrazines in the presence of metal ions such as $Fe^{2+}/Fe^{3+}$ and other hydrogen sources known from the prior art.

The reaction time for the asymmetric hydrogenation to be completed is generally between 2 and 48 hours, preferably between 4 and 36 hours, and particularly preferably about 23 hours.

The reaction of N-benzyl-salbutamone to obtain salbutamone is carried out by palladium-catalysed hydrogenating debenzylation. The reaction mixture from the asymmetric hydrogenation may be combined with a palladium catalyst without any further working up.

In this method benzylsalbutamone is combined with activated charcoal and a palladium chloride solution and hydrogenated under a pressure of more than 1 to 5 bar, preferably 2-3 bar. The further working up is carried out according to methods known from the literature.

The process according to the invention will now be illustrated by the Examples that follow. The skilled man will be aware that the examples are provided solely as an illustration and are not to be viewed as restrictive.

EXAMPLES

Example 1

Benzylsalbutamone 900 g of 4-acetyloxy-3-acetyloxymethylbenzophenone are placed in 6 l of suitable solvent. After the addition of 614 g bromine the mixture is refluxed for a further 30 minutes and cooled. After the addition of 1153 g of tert-butylbenzylamine the mixture is refluxed for another 20-25 h. After the precipitate has been filtered the organic phase is extracted with hydrochloric acid and the product is crystallised. 806 g of benzylsalbutamone are obtained.

Example 2

Salbutamone 36.4 g of benzylsalbutamone are taken up in 110 ml of water and stirred for 2.5 with 1 g of 10% Pd/C at 2 bar hydrogen pressure and at 40° C. The precipitate is dissolved with methanol. The solution is filtered through Celite and evaporated down until crystallisation starts. It is cooled overnight to ambient temperature and the crystals are filtered off. After washing with a little cold water and drying overnight at 50° C. in vacuo, salbutamone is obtained in a 92% yield.

Example 3

(R)-(−)-Salbutamol 10 g of salbutamone are dissolved in 100 ml of methanol (degassed) and 0.13 ml of triethylamine. 4.7 mg of (RhCODCl)2 and 10 mg of (2R,4R)-4-dicyclohexylphosphino)-2-(diphenylphosphino-methyl)-N-methyl-aminocarbonyl) pyrrolidine (as a toluenic solution) are added and the mixture is stirred for 23 h at 50° C. and 20 bar hydrogen pressure. The reaction solution is concentrated by rotary evaporation and the residue is recrystallised from ethanol. The salbutamol is obtained in a yield of 90% in an optical purity of approx. 70% e.e.

What is claimed is:

1. A process for preparing levosalbutamol or a pharmacologically acceptable salt thereof from prochiral salbutamone, comprising subjecting the salbutamone to asymmetric hydrogenation in the presence of rhodium and a chiral bidentate phosphine ligand as catalyst system and in the presence of a solvent comprising a protic or aprotic solvent, to obtain levosalbutamol, and optionally converting the resulting levosalbutamol into a salt with an acid.

2. The process according to claim 1, wherein the chiral bidentate phosphine ligand is (2R,4R)-4-(dicyclohexylphosphino)-2-(diphenylphosphino-methyl)-N-methyl-aminocarbonyl-pyrrolidine.

3. The process according to claim 1, wherein the chiral bidentate phosphine ligand is polymer-bound (2R,4R)-4-(dicyclohexylphosphino)-2-(diphenylphosphino-methyl)-N-methyl-aminocarbonyl-pyrrolidine.

4. The process according to claim 1, wherein the asymmetric hydrogenation is carried out in a temperature range from 20° C. to 100° C.

5. The process according to claim 4, wherein the asymmetric hydrogenation is carried out in a temperature range from 40° C. to 60° C.

6. The process according to claim 5, wherein the asymmetric hydrogenation is carried out in a temperature range from 45° C. to 55° C.

7. The process according to claim 1, wherein the asymmetric hydrogenation is carried out under a pressure of more than 1 bar to 100 bar.

8. The process according to claim 7, wherein the asymmetric hydrogenation is carried out under a pressure of about 20 bar.

9. The process according to claim 1, wherein the asymmetric hydrogenation is carried out in a protic solvent.

10. The process according to claim 9, wherein the asymmetric hydrogenation is carried out in a branched or unbranched $C_1$-$C_8$-alkanol as solvent.

11. The process according to claim 10, wherein the asymmetric hydrogenation is carried out in methanol, ethanol, n-propanol and/or isopropanol as solvent.

12. The process according to claim 11, wherein the solvent for the asymmetric hydrogenation additionally contains water.

13. The process according to claim 1, wherein, during asymmetric hydrogenation, salbutamone is used in a molar ratio to the rhodium catalyst of from 500:1 to 100000:1.

14. The process according to claim 13, wherein the molar ratio of salbutamone to the rhodium catalyst during asymmetric hydrogenation is about 1000: 1.

15. The process according to claim 1, wherein the rhodium catalyst for the asymmetric hydrogenation is used as a pre-prepared solution.

16. The process according to claim 1, wherein the rhodium catalyst for the asymmetric hydrogenation is produced in situ.

17. The process according to claim 1, wherein the asymmetric hydrogenation is carried out within a reaction time of 2 to 48 hours.

18. The process according to claim 17, wherein the reaction time for the asymmetric hydrogenation is about 23 hours.

19. The process according to claim 1, wherein the salbutamone is prepared starting from N-benzylsalbutamone by hydrogenation in the presence of a palladium catalyst.

20. The process according to claim 1 wherein:
   the asymmetric hydrogenation is carried out under a pressure of 10 to 50 bar;
   the salbutamone is used in a molar ratio to the rhodium catalyst of from 750:1 to 20000:1; and
   the reaction time is 4 to 36 hours.

21. A process for preparing levosalbutamol or a pharmacologically acceptable salt thereof, comprising:
   (a) brominating 4-acetyloxy-3-acetyloxymethylbenzophenone,
   (b) reacting the product obtained with N-tert-butyl-N-benzylamine to obtain N-benzylsalbutamone,
   (c) hydrogenating the N-benzylsalbutamone obtained in the presence of a palladium catalyst to obtain salbutamone, (d) hydrogenating the salbutamone obtained in the presence of rhodium and a chiral bidentate phosphine ligand and in the presence of a solvent comprising a protic or aprotic solvent, to obtain levosalbutamol, and (e) optionally treating the obtained levosalbutamol it with an acid to obtain a salt thereof.

22. The process according to claim 1, wherein the asymmetric hydrogenation is also carried out in the presence of a base.

23. The process of claim 22, wherein the base is an alkali metal carbonate or alkali metal hydroxide.

24. The process of claim 1, wherein the resulting levosalbutamol is converted into a salt with an acid and then the resulting salt is precipitated from an ammonia-methanol-water mixture.

25. The process of claim 1, wherein the levosalbutamol is obtained in an optical purity of at least 70% ee.

* * * * *